United States Patent [19]

Cho et al.

[11] Patent Number: 5,326,785
[45] Date of Patent: Jul. 5, 1994

[54] CAFFEIC ACID DERIVATIVES AND PHARMACEUTICAL COMPOSITIONS CONTAINING THE SAME

[75] Inventors: Hidetsura Cho, Ibaraki; Mie Tamaoka, Uda; Seiitsu Murota; Ikuo Morita, both of Tokyo, all of Japan

[73] Assignee: Suntory Limited, Osaka, Japan

[21] Appl. No.: 40,604

[22] Filed: Mar. 31, 1993

Related U.S. Application Data

[63] Continuation of Ser. No. 750,396, Aug. 27, 1991, Pat. No. 5,232,941.

[30] Foreign Application Priority Data

Aug. 30, 1990 [JP] Japan ................................. 2-26493

[51] Int. Cl.$^5$ ..................... C07D 317/08; A61K 31/21
[52] U.S. Cl. ................................. 514/465; 514/521; 549/442; 558/398; 558/399; 558/400
[58] Field of Search ....................... 558/398, 399, 400; 514/521, 465; 549/442

[56] References Cited

PUBLICATIONS

Chemical Abstracts, vol. 112, No. 21, Abstract No. 197,871v, p. 663, May 21, 1990.

*Primary Examiner*—C. Warren Ivy
*Assistant Examiner*—Zinna N. Davis
*Attorney, Agent, or Firm*—Oblon, Spivak, McClelland, Maier & Neustadt

[57] ABSTRACT

Described are caffeic acid derivatives represented by the following formula:

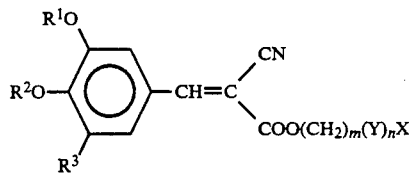

wherein either one of $R^1$ and $R^2$ is a hydrogen atom, a $C_1$-$C_6$ alkyl group, a group —$CO_2R^4$, or a group —$CONR^5R^6$, $R^4$, $R^5$ and $R^6$ being either a hydrogen atom or a particular group, and the other is the group —$CO_2R^4$ or the group —$CONR^5R^6$, or $R^1$ and $R^2$ are coupled together to represent a 5-membered ring so formed, Y represents a particular group or atom, X represents a substituted or unsubstituted $C_6$-$C_{10}$ aryl, $C_7$-$C_{12}$ aralkyl, heterocyclic or heterocyclic ring-alkyl group, m and n stand for particular integers, and $R^3$ represents a hydrogen atom, a hydroxyl group, a group —$OCO_2R^7$, $R^7$ being a hydrogen atom or a particular group, or a group —$OCONR^8R^9$, $R^8$ representing a $C_1$-$C_6$ alkyl group and $R^9$ representing a hydrogen atom or a $C_1$-$C_6$ alkyl group, and pharmaceutically acceptable salts thereof. Therapeutic agents containing the derivatives or salts are effective for diseases of the circulatory system.

2 Claims, No Drawings

CAFFEIC ACID DERIVATIVES AND PHARMACEUTICAL COMPOSITIONS CONTAINING THE SAME

This is a continuation of application Ser. No. 07/750,396, filed on Aug. 27, 1991, now U.S. Pat. No. 5,232,941.

BACKGROUND OF THE INVENTION

1) Field of the Invention

The present invention relates to novel caffeic acid derivatives, and more specifically to novel caffeic acid derivatives having 12-lipoxygenase inhibitory action and useful for the prevention and treatment of diseases of the circulatory system, such as arteriosclerosis, and medicines containing the derivatives as effective ingredients.

2) Description of the Related Art

Leukotriene which is considered to be a cause for allergic diseases, especially for asthma is known to be formed in the course of the conversion of arachidonic acid to 5-hydroperoxyeicosatetraenoic acid (5-HPETE) and 5-hydroxyeicosatetraenoic acid (5-HETE) under the action of 5-lipoxygenase.

Based on the findings, compounds having 5-lipoxygenase inhibition activity have been investigated with a view toward developing therapeutic agents for diseases of the circulatory system, resulting in many reports.

On the other hand, it is also known that 12-hydroperoxyeicosatetraenoic acid (12-HPETE) and 12-hydroxyeicosatetraenoic acid (12-HETE) are formed from arachidonic acid by another enzyme, 12-lipoxygenase. Regarding effects of these products on organisms, there are the report by Tada et al. that 12-HETE takes part in the development of ischemic heart disease [Cardiovascular Research, 21(8), 551–558 (1987)] and the report by Murota et al. that 12-HETE exhibits deteriorating action for endothelial cell diseases and wandering stimulating action for vascular tunica media smooth muscle cells and takes part in the increase and deterioration of vascular diseases such as arteriosclerosis and nephritis [Chiryogaku (Therapy), 13(6), 785–788 (1984)]. From the above findings, compounds having 12-lipoxygenase inhibitory action are expected to have utility as therapeutic agents for diseases of the circulatory system.

Compounds conventionally known to have 12-lipoxygenase inhibitory action include baicalein isolated from *Scutellaria baicalensis* and represented by the following formula:

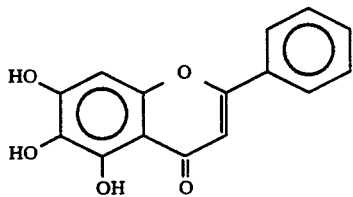

Although baicalein has 12-lipoxygenase inhibitory action, it is difficult to obtain it in large quantity as it is a natural product. Baicalein is therefore not suited for use as a medicine, leading to a desire for the development of a new inhibitor which can be produced by chemical synthesis.

With the foregoing in view, Cho, Murota and others—inventors of the present invention—have synthesized a variety of compounds and investigated their pharmacological effects. As a result, it was found that some of the compounds have 12-lipoxygenase inhibitory action. Some patent applications have already been filed on such compounds (Japanese Patent Application Laid—Open No. 275552/1989, Japanese Patent Application No. 55867/1989, etc.).

SUMMARY OF THE INVENTION

The present inventors have subjected to further screening the compounds having 12-lipoxygenase inhibitory action. As a result, it has been found that caffeic acid derivatives represented by the below-described formula (I) have inhibitory action at least comparable with baicalein, feature long acting property and low toxicity and permit large quantity synthesis, leading to the completion of the present invention.

Namely, the present invention provides a caffeic acid derivative represented by the following formula (I):

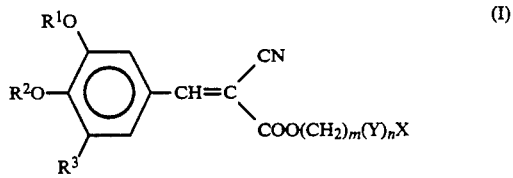

wherein $R^1$ and $R^2$ are independent from each other and either one of $R^1$ and $R^2$ is a hydrogen atom, a $C_1$–$C_6$ alkyl group, a group —$CO_2R^4$, $R^4$ representing a $C_1$–$C_{12}$ alkyl group, a $C_6$–$C_{10}$ aryl group, a hydrogen atom or a $C_7$–$C_{12}$ aralkyl group, or a group —$CONR^5R^6$, $R^5$ representing a $C_1$–$C_6$ alkyl group and $R^6$ a hydrogen atom or a $C_1$–$C_6$ alkyl group and the other is the group —$CO_2R^4$ or the group —$CONR^5R^6$, or $R^1$ and $R^2$ are coupled together to represent a 5-membered ring so formed, Y represents a vinylene group, an oxygen atom or a sulfur atom, X represents a substituted or unsubstituted $C_6$–$C_{10}$ aryl group, a substituted or unsubstituted $C_7$–$C_{12}$ aralkyl group, a substituted or unsubstituted heterocyclic group or a substituted or unsubstituted heterocyclic ring-alkyl group, m means an integer of 0–8, n denotes an integer of 0 or 1, and $R^3$ represents a hydrogen atom, a hydroxyl group, a group —$OCO_2R^7$, $R^7$ representing a $C_1$–$C_{12}$ alkyl group, a $C_6$–$C_{10}$ aryl group, a hydrogen atom or a $C_7$–$C_{12}$ aralkyl group, or a group —$OCONR^8R^9$, $R^8$ representing a $C_1$–$C_6$ alkyl group and $R^9$ representing a hydrogen atom or a $C_1$–$C_6$ alkyl group, or a pharmaceutically acceptable salt thereof; and also a therapeutic composition comprising the derivative as an effective ingredient.

Caffeic acid derivatives of the formula (I) and their pharmaceutically acceptable salts have excellent 12-lipoxygenase inhibitory activity so that they can be used as medicines, for example, therapeutic agents for diseases of the circulatory system.

DESCRIPTION OF THE INVENTION AND PREFERRED EMBODIMENT

In the formula (I), examples of the $C_1$–$C_6$ alkyl group include methyl, ethyl, propyl, isopropyl, butyl, isobutyl, sec-butyl, tert-butyl, pentyl, isopentyl, neopentyl, tert-pentyl, hexyl and isohexyl groups. Exemplary $C_1$–$C_{12}$ alkyl groups include methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl and dodecacyl groups.

Illustrative of the $C_6$-$C_{10}$ aryl group include phenyl and naphthyl groups, while the $C_7$-$C_{12}$ aralkyl group may be, for example, a benzyl, phenethyl, phenylpropyl, 1-phenylpropyl, 2-phenylpropyl, phenylbutyl, 1-phenylbutyl or naphthylmethyl group.

Further, exemplary heterocyclic groups include thienyl, thiazolyl, isothiazolyl, furyl, oxazolyl, isoxazolyl, pyranyl, pyrrolyl, imidazolyl, pyridyl, pyradinyl, pyrimidinyl, pyridazinyl and indolyl groups.

As the alkyl group of the heterocyclic ring-alkyl group, a straight or branched alkyl group having 1-6 carbon atoms can be used. As its examples, the above-described exemplary $C_1$-$C_6$ alkyl groups can be mentioned. Incidentally, examples of substituents on the aryl, $C_7$-$C_{12}$ aralkyl, heterocyclic and heterocyclic ring-alkyl group represented by X include $C_1$-$C_5$ alkyl groups, hydroxyl group, thiol group, acyl group, amino group, acylamino group, halogen atoms, cyano group, $C_1$-$C_5$ alkoxyl groups, carboxyl group and nitro group.

The caffeic acid derivative (I) of the present invention can be synthesized, for example, by the following processes:

Process A

In accordance with the below-described reaction scheme, an alcohol (II) and a cyanoacetic acid (III) are condensed into a cyanoacetate ester (IV), to which a benzaldehyde derivative (V) is reacted to obtain a compound (VI). Further reaction of this compound with a carbonyl compound (VII) or methylene iodide (VIII) can synthesize a caffeic acid derivative (Ia):

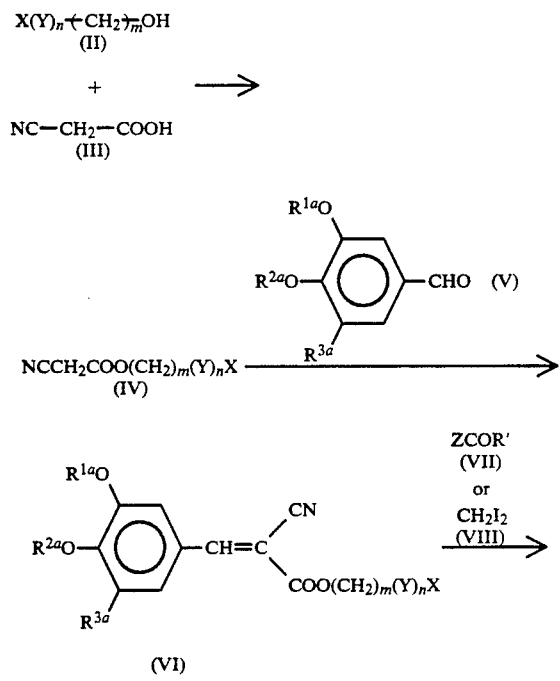

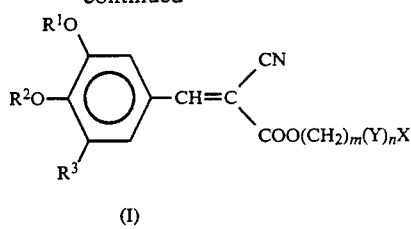

(I)

wherein $R^{1a}$ and $R^{2a}$ are independent from each other and either one of $R^{1a}$ and $R^{2a}$ is a $C_1$-$C_6$ alkyl group or a hydrogen atom and the other represents a hydrogen atom, $R^{3a}$ represents a hydrogen atom or a hydroxyl group, Z represents an easily removable group such as a halogen atom or a mesyl or tosyl group, R' denotes —$OR^4$, $R^4$ having the same meaning as defined above, —$NR^5R^6$, $R^5$ and $R^6$ having the same meanings as defined above, or Z, and $R^1$, $R^2$, $R^3$, X, Y, m and n have the same meanings as defined above.

The alcohol (II) as the starting material is a compound which is either available on the market or obtainable in a manner known per se in the art. Its examples include phenol, naphthol, benzyl alcohol, phenethyl alcohol, phenylpropanol, 1-phenylpropanol, 2-phenylpropanol, 3-phenyl-2-propanol, phenylbutanol, 1-phenylbutanol, 4-phenyl-2-butenol, 4-phenyl-1,3-butadienol, naphthylmethanol, phenoxymethanol, phenoxyethanol, phenoxypropanol, benzyloxymethanol, benzyloxyethanol, thiophenol, thienylmethanol, thienylethanol, thienylpropanol, thiazolol, thiazolylethanol, isothiazolol, isothiazolylethanol, furanol, furylmethanol, furylethanol, furylpropanol, oxazolol, oxazolyletanol, isooxazolol, isooxazolylethanol, pyranol, pyranylethanol, pyrrolol, pyrrolylethanol, imidazolol, imidazolylethanol, pyridinol, pyridylmethanol, pyridylethanol, pyridylpropanol, pyrazinol, pyrazinylethanol, pyrimidinol, pyrimidinylethanol, pyridazinol, pyridazinylethanol, indolol, and indolylethanol.

The condensation reaction between the alcohol (II) and the cyanoacetic acid (III) can be carried out by, if one or more functional groups are contained in the alcohol (II), protecting the alcohol (II) as needed and then using a condensing agent such as 1-ethyl-3-(3-dimethylaminopropyl)-carbodiimide or dicyclohexylcarbodiimide in a solvent inert to the reaction, for example, dimethylformamide in the presence of a base such as pyridine or piperidine. This reaction can be completed by using the cyanoacetic acid (III) in an amount approximately equivalent to the alcohol (II) and reacting them overnight or so at room temperature.

The reaction between the cyanoacetate ester (IV), which has been obtained by the above reaction, and the benzaldehyde derivative (V) is conducted, for example, by using a Dean-Stark apparatus or the like and subjecting the reactants to the conventional Knoevenagel condensation reaction, that is, heating the reactants under reflux for about 2 hours in a solvent inert to the reaction, for example, in an organic solvent such as benzene or toluene while using as a catalyst a base, for example, pyridine or piperidine, whereby the compound (VI) is obtained.

Examples of the benzaldehyde derivative (V) useful here include 3,4-dihydroxybenzaldehyde, 3,4,5-trihydroxybenzaldehyde, 3-hydroxy-4-methoxybenzaldehyde, 4-hydroxy-3-methoxybenzaldehyde, 4,5-dihydroxy-3-methoxybenzaldehyde.

When one or more functional groups in the group of the compound (VI) are protected, it is preferred to remove the protecting groups by a suitable method.

The reaction between the compound (VI) and the carbonyl compound (VII) is conducted by reacting the compound (VI) together with a suitable base, for example, a metal hydride reagent such as sodium hydride or potassium hydride, an inorganic base such as potassium carbonate or an organic base such as triethylamine at 0° C. to room temperature in the presence of an organic solvent inert to the reaction, for example, tetrahydrofuran (THF), dimethylsulfoxide (DMSO), sulfolane or dimethylformamide (DMF), followed by the further reaction with the carbonyl compound (VII) or methylene iodide (VIII) to obtain the desired compound (I).

When one or more functional groups are protected in the compound (I), the protecting groups can be removed by a suitable method.

The carbonyl compound (VII) usable here can be a haloformate derivative [in the formula (VII), R': —OR$^4$], a carbamoyl halide derivative [in the formula (VII), R': —NR$^5$R$^6$], or phosgene [in the formula (VII), R=Z=Cl] or the like.

Of these, exemplary haloformate derivatives include alkyl chloroformates such as methyl chloroformate, ethyl chloroformate and nonyl chloroformate, aryl chloroformates such as phenyl chloroformate, and aralkyl chloroformates such as benzyl chloroformate and phenethyl chloroformate.

On the other hand, exemplary carbamoylhalide derivatives include alkylcarbamoyl chlorides such as dimethylcarbamoyl chloride, ethylmethylcarbamoyl chloride and diethylcarbamoyl chloride.

Where R$^6$ is a hydrogen atom in the group —NR$^5$R$^6$ of the desired compound (I), an isocyanate represented by the following formula:

$$R^5-N=C=O$$

wherein R$^5$ has the same meaning as defined above can be used. Examples of such isocyanates include alkyl isocyanates such as methyl isocyanate, ethyl isocyanate and propyl isocyanate.

By adjusting the amount of the carbonyl derivative (VII) other than phosgene to 1–5 equivalents upon reaction, it is possible to selectively form the compound (I) of the present invention in which any one or two or all of —R$^3$, —OR$^1$ and —OR$^2$ have been substituted by the carbonyl compound.

On the other hand, reaction of phosgene [in formula (VII), R=Z=Cl] or its related compounds with the compound (VI) results in the synthesis of a compound (Ia') represented by the below-described formula whereas reaction of methylene iodide (VIII) or the like with the compound (VI) similarly leads to the synthesis of a compound (Ia") represented by the below-described formula.

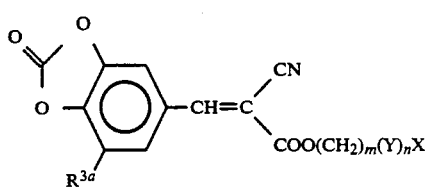

(Ia')

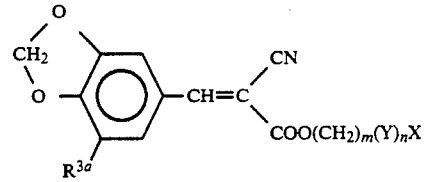

(Ia")

Process B

A caffeic acid derivative (Ib) can be synthesized by reacting phosgene (or its related compounds) with the compound (VI'), which has been obtained by the process A, and then reacting an amine compound represented by the formula (X):

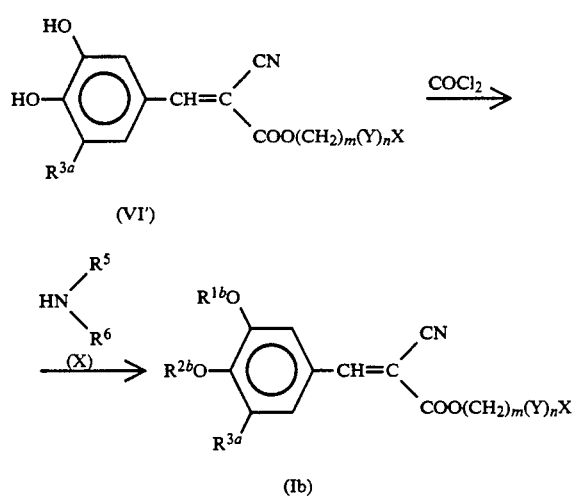

wherein R$^{1b}$ and R$^{2b}$ are independent from each other and either one of R$^{1b}$ and R$^{2b}$ is a hydrogen atom and a group —CONR$^5$R$^6$ and the other represents a group —CONR$^5$R$^6$, and R$^{3a}$, R$^5$, R$^6$, X, Y, m and n have the same meanings as defined above.

More substituents can be introduced into the caffeic acid derivative (Ib) by reacting the compound (VII) or (VIII) to the caffeic acid derivative (Ib) in a similar manner to Process A.

The above reaction is carried out by reacting the compound (VI') together with a suitable base, for example, a metal hydride reagent such as sodium hydride or potassium hydride, an inorganic base such as potassium carbonate or an organic base such as triethylamine at 0° C. to room temperature in the presence of an organic solvent inert to the reaction, for example, tetrahydrofuran (THF), dimethylsulfoxide (DMSO), sulfolane or dimethylformamide (DMF), followed by the reaction with phosgene (or its related compounds) and further by the reaction with the amine compound (X).

Examples of the amine compound (X) used in the above reaction include alkylamines such as methylamine, ethylamine, propylamine, dimethylamine, diethylamine and ethylmethylamine.

Purification of each compound (I) of the present invention obtained as described above can be effected by cooling the reaction mixture and then collecting precipitated crystals by filtration or by subjecting the resultant compound to purification such as recrystallization or chromatography on a silica gel column.

If desired, each caffeic acid derivative (I) according to the present invention can be converted to a pharmaceutically acceptable salt, for example, to a base addition salt usable as a medicine such as the sodium, potassium or calcium salt.

Pharmacological effects of certain compounds (I) of the present invention, which had been obtained in a manner as described above, were tested. The results will be described next.

Pharmaceutical Effects (1) 12-Lipoxygenase inhibition activity (in vitro)

The 12-lipoxygenase inhibition activity of each test compound according to the present invention was measured in the following manner.

Firstly, blood was collected from the heart of a rat (while using sodium citrate as an anticoagulant), and platelet rich plasma was prepared by a method known per se in the art. The platelet rich plasma was washed twice with a isotonic buffer (A) 134 mM of NaCl, 5 mM of D-glucose, 1 mM of EDTA, 1 mM of EGTA, 15 mM of tris-HCl (pH 7.4)] and was then frozen and stored at $-80°$ C. Prior to a pharmacological test, the frozen platelet rich plasma was allowed to melt and then subjected to ultrasonic treatment in ice water so that an enzyme solution was obtained. To the isotonic buffer (A), 1 mM of GSH, the test compound (adjusted to have the final concentrations of 1 $\mu$M and 0.1 $\mu$M) and the enzyme solution (300–500 $\mu$g of protein) were added. Subsequent to pre-incubation at 37° C. for 5 minutes, [$^{14}$C]-arachidonic acid (0.05 $\mu$Ci) (final concentration: 4.3M) was added to react it for 5 minutes. After the reaction was terminated, the reaction mixture was spread over a thin layer plate of silica gel to conduct autoradiography. 12-HETE was identified and a reduction in its production was determined as an index for its 12-lipoxygenase inhibition activity.

The inhibition rates (%) of 12-HETE production suppressed by the compounds of the present invention are summarized in the following table:

| Compound No. | Inhibition rate (%) $10^{-7}$ M | Inhibition rate (%) $10^{-6}$ M |
|---|---|---|
| 1 | 52.9 | 85.4 |
| 6 | 60.3 | |
| 7 | 40.8 | 75.6 |
| 8 | 9.4 | 65.1 |
| 9 | 4.2 | 71.8 |
| 10 | 38.7 | 79.3 |
| 11 | 23.5 | 53.8 |
| 12 | 16.3 | 68.4 |
| 13 | — | 40.8 |
| 14 | 34.6 | 64.6 |
| 17 | 59.3 | 75.9 |
| 18 | 65.8 | |
| 19 | 4.6 | 50.8 |
| 20 | 41.2 | 63.4 |
| 21 | — | 41.6 |
| 22 | 14.0 | 27.6 |
| 23 | 64.5 | 84.5 |
| 29 | 25.1 | 59.2 |
| 34 | 91.5 | |
| 35 | 56.6 | 82.9 |
| 36 | 75.6 | |

(—: No activity)

(2) 12-Lipoxygenase inhibition activity in platelets (extro vivo)

Under anesthesia with pentobarbital, an SD rat (8 week-old, male) was intravenously administered with a polyethylene glycol solution containing 1.0 mg/kg of a test compound. Ten minutes after the administration, blood was collected from the abdominal vena cava, and the inhibitory activity was measured as in the above test (1).

Setting at 100% the amount of 12-HETE of the group in which a base preparation was administered instead of the drugs, the results, namely, the amount of 12-HETE obtained when each test drug was administered was indicated in terms of %. As a result, Compound 1 showed 30% inhibitory effect while Compound 17 exhibited 18% inhibitory effect.

As has been demonstrated above, the caffeic acid derivatives (I) according to the present invention have excellent 12-lipoxygenase inhibitory activity so that they can be used as medicines, for example, therapeutic agents for diseases of the circulatory system.

To use each caffeic acid derivative (I) of the present invention as a medicine such as a therapeutic agent for diseases of the circulatory system, the compound or its pharmaceutically acceptable salt is formulated either alone or in combination with a known, non-toxic excipient or the like into a suitable preparation form permitting its oral or parenteral administration such as capsules, tablets or an injectable preparation.

These preparations can be formulated, for example, in the following manner. The compound (I) of this invention is triturated alone, mixed with an excipient, e.g., lactose, starch or its derivative, a cellulose derivative or the like, and then filled in gelatin capsules to form capsules.

To formulate tablets, a binder—such as carboxymethylcellulose sodium, alginic acid or gum arabic—and water are added beside the excipient and the resulting mixture is kneaded and, if necessary, is formed into granules. A lubricant such as talc or stearic acid is added further and is then formed into tablets by a conventional compressed tablet machine. To formulate a parenterally-dosable, i.e., injectable preparation, the compound (I) of the present invention is dissolved together with a solubilizer in sterilized distilled water or sterilized physiological saline and is then filled in ampoules to provide an injectable preparation. Here, a stabilizer and/or a buffer substance may be added as needed.

The effective amount of each therapeutic agent of the present invention for a disease of the circulatory system varies depending on the kind of the disease, the severity of the condition, the administration method, and physical factors of the patient. In general, the therapeutic agent can be administered in an amount sufficient to lessen the symptom of the disease. As an example, it is preferred to administer the compound (I) of the present invention to an adult at a daily dosage of 1–1,000 mg or so.

The caffeic acid derivatives (I) according to the present invention have not only 5-lipoxygenase inhibitory action but also 12-lipoxygenase inhibitory action, so that they are useful as therapeutic agents for diseases of the circulatory system, for example, for the prevention of arterioscherosis.

The present invention will hereinafter be described in further detail. It should however be borne in mind that the present invention is not limited at all by the following examples.

EXAMPLE 1

Synthesis of phenethyl 2-cyano-3-(3,4-diethoxycarbonyloxyphenyl)-2-propenoate (Compound 1)

500 mg (10.4 mmol) of 50% sodium hydride were washed with hexane to remove mineral oil, followed by the addition of 5 ml of dry THF. Under a nitrogen gas stream, a solution of 1.48 g (4.8 mmol) of phenethyl 2-cyano-3-(3,4-dihydroxyphenyl)-2-propenoate in 15 ml of dry THF was added at 0° C. and 950 μl (9.9 mmol) of ethyl chloroformate were then added.

After being stirred at 0° C. for 5 minutes, they were reacted at room temperature for 1 hour and the solvent was distilled out. Water was added and the mixture was extracted with chloroform. The organic layer was dried over anhydrous magnesium sulfate and the solvent was distilled out under reduced pressure. The residue was purified by chromatography on a silica gel column (hexane:chloroform=1:9) and recrystallized from hexane-chloroform, whereby the title compound was obtained in an amount of 1.80 g (83%).

Use of phenethyl 2-cyano-3-(4-hydroxy-3-methoxyphenyl)-2-propenoate, phenethyl 2-cyano-3-(3-hydroxy-4-methoxyphenyl)-2-propenoate, phenyl 2-cyano-3-(3,4-dihydroxyphenyl)-2-propenoate, phenyl 2-cyano-3-(4-hydroxy-3-methoxyphenyl)-2-propenoate, ethyl 2-cyano-3-(3,4-dihydroxyphenyl)-2-propenoate, (S)-(−)-1-phenylbutyl 2-cyano-3-(3,4-dihydroxyphenyl)-2-propenoate, (R)-(+)-1-phenylbutyl 2-cyano-3-(3,4-dihydroxyphenyl)-2-propenoate, 1-methyl-2-phenylethyl 2-cyano-3-(3,4-dihydroxyphenyl)-2-propenoate, 2-(3-thienyl)-ethyl 2-cyano-3-(3,4-dihydroxyphenyl)-2-propenoate, 2-furylmethyl 2-cyano-3-(3,4-dihydroxyphenyl)-2-propenoate, 3-(2-pyridyl)-propyl 2-cyano-3-(3,4-dihydroxyphenyl)-2-propenoate, 3-(3-pyridyl)-propyl 2-cyano-3-(3,4-dihydroxyphenyl)-2-propenoate, 3-thienylmethyl 2-cyano-3-(3,4-dihydroxyphenyl)-2-propenoate, 2-(2-thienyl)-ethyl 2-cyano-3-(4-hydroxy-3-methoxyphenyl-2-propenoate and 2-(2-thienyl)-ethyl 2-cyano-3-(3-hydroxy-4-methoxyphenyl)-2-propenoate in lieu of phenethyl 2-cyano-3-(3,4-dihydroxyphenyl)-2-propenoate in the above-described manner provided phenethyl 2-cyano-3-(4-ethoxycarbonyloxy-3-methoxyphenyl)-2-propenoate (Compound 2), phenethyl 2-cyano-3-(3-ethoxycarbonyloxy-4-methoxyphenyl)-2-propenoate (Compound 3), phenyl 2-cyano-3-(3,4-diethoxycarbonyloxyphenyl)-2-propenoate (Compound 4), phenyl 2-cyano-3-(4-ethoxycarbonyloxy-3-methoxyphenyl)-2-propenoate (Compound 5), ethyl 2-cyano-3-(3,4-diethoxycarbonyloxyphenyl)-2-propenoate (Compound 6), (S)-(-)-1-phenylbutyl 2-cyano-3-(3,4-diethoxycarbonyloxyphenyl)-2-propenoate (Compound 7), (R)-(+)-1-phenylbutyl 2-cyano-3-(3,4-diethoxycarbonyloxyphenyl)-2-propenoate (Compound 8), 1-methyl-2-phenylethyl 2-cyano-3-(3,4-diethoxycarbonyloxyphenyl)-2-propenoate (Compound 9), 2-(3-thienyl)-ethyl 2-cyano-3-(3,4-diethoxycarbonyloxyphenyl)-2-propenoate (Compound 10), 2-furylmethyl 2-cyano-3-(3,4-diethoxycarbonyloxyphenyl)-2-propenoate (Compound 11), 3-(2-pyridyl)-propyl 2-cyano-3-(3,4-diethoxycarbonyloxyphenyl)-2-propenoate (Compound 12), 3-(3-pyridyl)-propyl 2-cyano-3-(3,4-diethoxycarbonyloxyphenyl)-2-propenoate (Compound 13), 3-thienylmethyl 2-cyano-3-(3,4-diethoxycarbonyloxyphenyl)-2-propenoate (Compound 14), 2-(2-thienyl)-ethyl 2-cyano-3-(4-ethoxycarbonyloxy-3-methoxyphenyl)-2-propenoate (Compound 15) and 2-(2-thienyl)-ethyl 2-cyano-3-(3-ethoxycarbonyloxy-4-methoxyphenyl)-2-propenoate (Compound 16), respectively.

Further, reduction of the amount of ethyl chloroformate to ½ in the above-described process selectively provided phenethyl 2-cyano-3-(3-ethoxycarbonyloxy-4-hydroxyphenyl)-2-propenoate (Compound 17).

EXAMPLE 2

Synthesis of 2-(2-thienyl)-ethyl 2-cyano-3-(3,4-diethoxycarbonyloxyphenyl)-2-propenoate (Compound 18)

Use of 2-(2-thienyl)-ethyl 2-cyano-3-(3,4-dihydroxyphenyl)-2-propenoate in place of phenethyl 2-cyano-3-(3,4-dihydroxyphenyl)-2-propenoate in the process of Example 1 provided the title compound.

When methyl chloroformate, isobutyl chloroformate, benzyl chloroformate and heptyl chloroformate were separately used instead of ethyl chloroformate in a similar manner to the process described above, 2-(2-thienyl)-ethyl 2-cyano-3-(3,4-dimethoxycarbonyloxyphenyl)-2-propenoate (Compound 19), 2-(2-thienyl)-ethyl 2-cyano-3-(3,4-diisobutoxycarbonyloxyphenyl)-2-propenoate (Compound 20), 2-(2-thienyl)-ethyl 2-cyano-3-(3,4-dibenzyloxycarbonyloxyphenyl)-2-propenoate (Compound 21) and 2-(2-thienyl)-ethyl 2-cyano-3-(3,4-diheptoxycarbonyloxyphenyl)-2-propenoate (Compound 22) were obtained.

Further, reduction of the amount of ethyl chloroformate to ½ in a similar manner to the process described above selectively provided 2-(2-thienyl)-ethyl 2-cyano-3-(3-ethoxycarbonyloxy-4-hydroxyphenyl)-2-propenoate (Compound 23).

By using 2-pyridylethyl 2-cyano-3-(3,4-dihydroxyphenyl)-2-propenoate, 8-(imidazol-1-yl)-octanyl 2-cyano-3-(3,4-dihydroxyphenyl)-2-propenoate, 4-aminophenethyl 2-cyano-3-(3,4-dihydroxyphenyl)-2-propenoate, phenoxyethyl 2-cyano-3-(3,4-dihydroxyphenyl)-2-propenoate and cinnamyl 2-cyano-3-(3,4-dihydroxyphenyl)-2-propenoate instead of phenethyl 2-cyano-3-(3,4-dihydroxyphenyl)-2-propenoate and 2.0–2.2 equivalents of ethyl chloroformate as an alkyl chloroformate and reacting them in a similar manner to the process of Example 1, 2-pyridylethyl 2-cyano-3-(3,4-diethoxycarbonyloxyphenyl)-2-propenoate (Compound 24), 8-(imidazol-1-yl)-octanyl 2-cyano-3-(3-ethoxycarbonyloxy-4-hydroxyphenyl)-2-propenoate (Compound 25), 4-aminophenethyl 2-cyano-3-(3,4-diethoxycarbonyloxyphenyl)-2-propenoate (Compound 26), phenoxyethyl 2-cyano-3-(3,4-diethoxycarbonyloxyphenyl)-2-propenoate (Compound 27) and cinnamyl 2-cyano-3-(3,4-diethoxycarbonyloxyphenyl)-2-propenoate (Compound 28) were obtained, respectively.

EXAMPLE 3

Synthesis of 2-(2-thienyl)-ethyl 2-cyano-3-(3,4,5-triethoxycarbonyloxyphenyl)-2-propenoate (Compound 29)

By using 2-(2-thienyl)-ethyl 2-cyano-3-(3,4,5-trihydroxyphenyl)-2-propenoate in lieu of phenyl 2-cyano-3-(3,4-dihydroxyphenyl)-2-propenoate and changing the amount of ethyl chloroformate to 3.3 equivalents in the process of Example 1, the title compound was obtained.

EXAMPLE 4

Synthesis of 2-(2-thienyl)-ethyl 2-cyano-3-(3,4-diethylcarbamoyloxyphenyl)-2-propenoate (Compound 30)

31 mg (0.10 mmol) of 2-(2-thienyl)-ethyl 2-cyano-3-(3,4-dihydroxyphenyl)-2-propenoate were dissolved in 2 ml of ethyl isocyanate, followed by the addition of 1 droplet of triethylamine. The resultant mixture was stirred at room temperature for 18 hours.

Excess reagents were distilled out under reduced pressure, and the residue was added and acidified with a 10% aqueous solution of hydrochloric acid, followed by extraction in chloroform. After the chloroform layer was dried over anhydrous magnesium sulfate, the chloroform solution was filtered and chloroform was distilled out under reduced pressure. Crude crystals so obtained were recrystallized from n-hexane-chloroform so that the title compound was obtained.

By adding 3–7 equivalents of triethylamine to a THF solution of the starting material, 2-(2-thienyl)-ethyl 2-cyano-3-(3,4-dihydroxyphenyl)-2-propenoate and adding 3 equivalents or 7 or more equivalents of N,N-dimethylcarbamoyl chloride instead of ethyl isocyanate, 2-(2-thienyl)-ethyl 2-cyano-3-(3-N,N-dimethylcarbamoyloxy-4-hydroxyphenyl)-2-propenoate (Compound 31) and 2-(2-thienyl)-ethyl 2-cyano-3-(3,4-di-N,N-dimethylcarbamoyloxyphenyl)-2-propenoate (Compound 32) were obtained, respectively.

By reacting Compound 31 with ethyl chloroformate in the presence of sodium hydride or triethylamine at 0° C. to room temperature in THF as a solvent in accordance with the process of Example 1, 2-(2-thienyl)-ethyl 2-cyano-3-(3—N,N-dimethylcarbamoyloxy-4-ethoxycarbonyloxyphenyl)-2-propenoate (Compound 33) was obtained.

EXAMPLE 5

Synthesis of 2-(2-thienyl)-ethyl 2-cyano-3-(3,4-cyclic dioxolonylphenyl)-2-propenoate (Compound 34)

250 mg (6.3 mmol) of 60% sodium hydride were washed with hexane, followed by the addition of 5 ml of dry THF. A solution of 680 mg (2.2 mmol) of 2-(2-thienyl)ethyl 2-cyano-3-(3,4-dihydroxyphenyl)-2-propenoate in 20 ml of dry THF was added at 0° C., to which 400 μl (3 3 mmol) of trichloromethyl chloroformate (phosgene dimer) were added. The resulting mixture was heated under reflux. Eighteen hours later, most of the solvent was distilled out under reduced pressure, and the residue was added with water and then extracted in chloroform. The organic layer was dried over anhydrous magnesium sulfate, dried, and then distilled out under reduced pressure. Hexane was added to crystallize the reaction product, followed by the recrystallization from chloroform-hexane to obtain 160 mg of the title compound (22%).

Separate use of phenethyl 2-cyano-3-(3,4-dihydroxyphenyl)-2-propenoate and phenyl 2-cyano-3-(3,4-dihydroxyphenyl)-2-propenoate instead of 2-(2-thienyl)-ethyl 2-cyano-3-(3,4-dihydroxyphenyl)-2-propenoate in a similar manner to the above-described process provided phenethyl 2-cyano-3-(3,4-cyclic dioxolonylphenyl)-2-propenoate (Compound 35) and phenyl 2-cyano-3-(3,4-cyclic dioxolonylphenyl)-2-propenoate (Compound 36), respectively.

Physicochemical data of the individual compounds obtained above in Examples 1–5 are as shown next in Tables 1–9.

TABLE 1

| Compound No. | Structure [in Formula (I)] R¹ | R² | R³ | —(CH$_2$)$_m$(Y)$_n$X | Yield | Property, m.p. (°C.) recrystallizing solvent | IR* (υcm$^{-1}$) | NMR** (δ ppm) |
|---|---|---|---|---|---|---|---|---|
| 1 | —CO$_2$Et | —CO$_2$Et | H | —CH$_2$CH$_2$—⟨C$_6$H$_4$⟩ | 83 | 98–99 CHCl$_3$-hexane | 1730 1770 2225 | 1.39(6H, t, J=7Hz), 3.07(2H, t, J=7Hz), 4.35(4H, q, J=7Hz), 4.52(2H, t, J=7Hz), 7.20–7.41(5H, m), 7.46(1H, d, J=9Hz), 7.90(1H, dd, J=9Hz, 2Hz), 7.94(1H, d, J=2Hz), 7.94(1H, d, J=2Hz), 8.14(1H, s). |
| 2 | —Me | —CO$_2$Et | H | —CH$_2$CH$_2$—⟨C$_6$H$_4$⟩ | 29 | 80–81 CHCl$_3$-hexane | 1730 1770 2225 | 1.40(3H, t, J=7Hz), 3.08(2H, t, J=7Hz), 3.94(3H, s), 4.34(2H, q, J=7Hz), 4.52(2H, t, J=7Hz), 7.19–7.41(6H, m), 7.43(1H, dd, J=9Hz, 2Hz), 7.83(1H, d, J=2Hz), 8.16(1H, s). |
| 3 | —CO$_2$Et | —Me | H | —CH$_2$CH$_2$—⟨C$_6$H$_4$⟩ | 65 | 91–92 CHCl$_3$-hexane | 1725 1765 2225 | 1.40(3H, t, J=7Hz), 3.06(2H, t, J=7Hz), 3.95(3H, s), 4.34(2H, q, J=7Hz), 4.49(2H, t, J=7Hz), 7.06(1H, d, J=9Hz), 7.15–7.45(5H, m), 7.85(1H, d, J=2Hz), 7.91(1H, dd, J=9Hz, 2Hz), 8.09(1H, s). |
| 4 | —CO$_2$Et | —CO$_2$Et | H | ⟨C$_6$H$_5$⟩ | 67 | Oil | 1745 1780 2230 | 1.40(6H, t, J=7Hz), 4.36(4H, q, J=7Hz), 7.18–7.55(6H, m), 7.93–8.09(2H, m), 8.33(1H, s). |

*IR was measured in CHCl$_3$ in principle.
**NMR was measured in CDCl$_3$ in principle.

TABLE 2

| Compound No. | Structure [in Formula (I)] R¹ | R² | R³ | —(CH$_2$)$_m$(Y)$_n$X | Yield | Property, m.p. (°C.) recrystallizing solvent | IR* (νcm$^{-1}$) | NMR** (δ ppm) |
|---|---|---|---|---|---|---|---|---|
| 5 | —Me | —CO$_2$Et | H |  | 68 | 108–110 CHCl$_3$-hexane | 1740 1765 2225 | 1.41(3H, t, J=7Hz), 3.96(3H, s), 4.35(2H, q, J=7Hz), 7.15–7.49(6H, m), 7.52(1H, dd, J=9Hz, 2Hz), 7.91(1H, d, J=2Hz), 8.35(1H, s). |
| 6 | —CO$_2$Et | —CO$_2$Et | H | —Et | 61 | 86–88 CHCl$_3$-hexane | 1730 1770 2225 | 1.25–1.48(9H, m), 4.27–4.48(6H, m), 7.46(1H, d, J=9Hz), 7.91(1H, dd, J=9Hz, 2Hz), 7.94(1H, d, J=2Hz), 8.19(1H, s). |
| 7 | —CO$_2$Et | —CO$_2$Et | H | *(S)-(−) —CH(C$_6$H$_5$)CH$_2$CH$_2$CH$_3$ | 90 | Oil | 1725 1760 2225 | 0.96(3H, t, J=7Hz), 1.12–1.52(8H, m), 1.78–1.97(1H, m), 1.97–2.16(1H, m), 4.34(4H, q, J=7Hz), 5.91(1H, t, J=7Hz), 7.27–7.54(6H, m), 7.87–8.01(2H, m), 8.15(1H, s). |
| 8 | —CO$_2$Et | —CO$_2$Et | H | *(R)-(+) —CH(C$_6$H$_5$)CH$_2$CH$_2$CH$_3$ | 60 | Oil | 1725 1770 2225 | 0.96(3H, t, J=7Hz), 1.12–1.52(8H, m), 1.78–1.97(1H, m), 1.97–2.16(1H, m), 4.34(4H, q, J=7Hz), 5.91(1H, t, J=7Hz), 7.27–7.54(6H, m), 7.87–8.01(2H, m), 8.15(1H, s). |

*IR was measured in CHCl$_3$ in principle.
**NMR was measured in CDCl$_3$ in principle.

TABLE 3

| Compound No. | Structure [in Formula (I)] R¹ | R² | R³ | —(CH$_2$)$_m$(Y)$_n$X | Yield | Property, m.p. (°C.) recrystallizing solvent | IR* (νcm$^{-1}$) | NMR** (δ ppm) |
|---|---|---|---|---|---|---|---|---|
| 9 | —CO$_2$Et | —CO$_2$Et | H | —CHCH$_2$—(phenyl) with CH$_3$ | 72 | Oil | 1725, 1770 | 1.10–1.48(9H, m), 2.90(1H, dd, J=14Hz, 6Hz), 3.05(1H, dd, J=14Hz, 7Hz), 4.35(4H, q, J=7Hz), 8.09(1H, s), 5.18–5.39(1H, m), 22.30 7.15–7.39(5H, m), 7.45(1H, d, J=9Hz), 7.97(1H, dd, J=2Hz), 7.93(1H, d, J=2Hz). |
| 10 | —CO$_2$Et | —CO$_2$Et | H | —CH$_2$CH$_2$—(thiophene) | 83 | 107–108 CHCl$_3$-hexane | 1730, 1770, 2225 | 1.40(6H, t, J=7Hz), 3.11(2H, t, J=7Hz), 4.35(4H, q, J=7Hz), 4.51(2H, t, J=7Hz), 7.05(1H, dd, J=5Hz, 1Hz), 7.12(1H, dd, J=3Hz, 1Hz), 7.30(1H, dd, J=5Hz, 3Hz), 7.46(1H, d, J=9Hz), 7.91(1H, dd, J=9Hz, 2Hz), 7.95(1H, d, J=2Hz), 8.16(1H, s). |
| 11 | —CO$_2$Et | —CO$_2$Et | H | —CH$_2$—(furan) | 94 | 113–114 CHCl$_3$-hexane | 1730, 1770, 2230 | 1.39(6H, t, J=7Hz), 4.34(4H, q, J=7Hz), 5.31(2H, s), 6.39(1H, dd, J=3Hz, 2Hz), 6.52(1H, d, J=3Hz), 7.42–7.46(2H, m), 7.89–8.06(2H, m), 8.19(1H, m). |
| 12 | —CO$_2$Et | —CO$_2$Et | H | —CH$_2$CH$_2$CH$_2$—(pyridine) | 6 | Powder | 1730, 1770, 2225 | 1.40(6H, t, J=7Hz), 2.15–2.34(2H, m), 2.96(2H, s), 4.22–4.43(6H, m), 7.08–7.24(2H, m), 7.46(1H, d, J=9Hz), 7.58–7.68(1H, m), 7.88–7.97(2H, m), 8.16(1H, s), 8.54(1H, dd, J=4Hz, 1Hz). |

*IR was measured in CHCl$_3$ in principle.
**NMR was measured in CDCl$_3$ in principle.

TABLE 4

| Compound No. | Structure [in Formula (I)] R¹ | R² | R³ | $-(CH_2)_m(Y)_nX$ | Yield | Property, m.p. (°C.) recrystallizing solvent | IR* (νcm⁻¹) | NMR** (δ ppm) |
|---|---|---|---|---|---|---|---|---|
| 13 | —CO₂Et | —CO₂Et | H | —CH₂CH₂CH₂— (3-pyridyl) | 72 | 99–100 CHCl₃-hexane | 1730 1770 2225 | 1.46(6H, t, J=7Hz), 2.03–2.19(2H, m), 2.80(2H, t, J=7Hz), 4.20–4.47(6H, m), 7.18–7.27(1H, m), 7.47(1H, d, J=9Hz), 7.51–7.61(1H, m), 7.89–8.00(2H, m), 8.16(1H, s), 8.41–8.55(2H, m). |
| 14 | —CO₂Et | —CO₂Et | H | —CH₂— (2-thienyl) | 93 | 120–122 CHCl₃-hexane | 1730 1770 | 1.39(6H, t, J=7Hz), 4.35(4H, q, J=7Hz), 5.36(2H, s), 7.17(1H, dd, J=5Hz, 1Hz), 7.35(1H, dd, J=5Hz, 3Hz), 7.41(1H, dd, J=3Hz, 1Hz), 2225 7.46(1H, d, J=9Hz), 7.91(1H, dd, J=9Hz, 2Hz), 7.94(1H, d, J=2Hz), 8.19(1H, s). |
| 15 | —Me | —CO₂Et | H | —CH₂CH₂— (2-thienyl) | 72 | 83–84 CHCl₃-hexane | 1730 1765 2225 | 1.40(3H, t, J=7Hz), 3.30(2H, t, J=7Hz), 3.93(3H, s), 4.34(2H, q, J=7Hz), 4.53(2H, t, J=7Hz), 6.85–7.06(2H, m), 7.19(1H, dd, J=5Hz, 1Hz), 7.27(1H, d, J=9Hz), 7.45(1H, dd, J=9Hz, 2Hz), 7.85(1H, d, J=2Hz), 8.20(1H, s). |
| 16 | —CO₂Et | —Me | H | —CH₂CH₂— (2-thienyl) | 66 | 91–92 CHCl₃-hexane | 1725 1765 2225 | 1.40(3H, t, J=7Hz), 3.29(2H, t, J=7Hz), 3.95(3H, s), 4.34(2H, q, J=7Hz), 4.51(2H, t, J=7Hz), 6.90–7.01(2H, m), 7.07(1H, d, J=9Hz), 7.19(1H, dd, J=5Hz, 1Hz), 7.87(1H, d, J=2Hz), 7.93(1H, dd, J=9Hz, 2Hz), 8.14(1H, s). |

*IR was measured in CHCl₃ in principle.
**NMR was measured in CDCl₃ in principle.

TABLE 5

| Compound No. | Structure [in Formula (I)] R¹ | R² | R³ | $-(CH_2)_m(Y)_nX$ | Yield | Property, m.p. (°C.) recrystallizing solvent | IR* ($vcm^{-1}$) | NMR** ($\delta$ ppm) |
|---|---|---|---|---|---|---|---|---|
| 17 | $-CO_2Et$ | H | H | $-CH_2CH_2-\text{(phenyl)}$ | 47 | 124–126 CHCl$_3$-hexane | 1730 1770 2230 | 1.42(3H, t, J=7Hz), 3.06(2H, t, J=7Hz), 4.38(2H, q, J=7Hz), 4.50(2H, t, J=7Hz), 7.10(1H, d, J=7Hz), 7.17–7.46(5H, m), 7.81(1H, dd, J=9Hz, 2Hz), 7.96(1H, d, J=2Hz), 8.09(1H, s). |
| 18 | $-CO_2Et$ | $-CO_2Et$ | H | $-CH_2CH_2-\text{(thienyl)}$ | 93 | 87–87 CHCl$_3$-hexane | 1730 1775 2230 | 1.39(6H, t, J=7Hz), 3.29(2H, t, J=7Hz), 4.35(4H, q, J=7Hz), 4.53(2H, q, J=7Hz), 6.89–7.02(2H, m), 7.19(1H, dd, J=5Hz, 1Hz), 7.46(1H, d, J=9Hz), 7.90(1H, dd, J=9Hz, 2Hz), 7.95(1H, d, J=2Hz), 8.18(1H, s). |
| 19 | $-CO_2Me$ | $-CO_2Me$ | H | $-CH_2CH_2-\text{(thienyl)}$ | 54 | 81–83 EtOH | 1730 1770 2225 | 3.30(2H, t, J=7Hz), 3.94(6H, s), 4.53(2H, t, J=7Hz), 6.84–7.07(2H, m), 7.19(1H, dd, J=5Hz, 1Hz), 7.47(1H, d, J=9Hz), 7.93(1H, dd, J=9Hz, 2Hz), 7.96(1H, d, J=2Hz), 8.18(1H, s). |
| 20 | $-CO_2CH_2-CH(CH_3)_2$ | $-CO_2CH_2-CH(CH_3)_2$ | H | $-CH_2CH_2-\text{(thienyl)}$ | 42 | 56–57 CHCl$_3$-hexane | 1730 1770 2230 | 1.00(12H, d, J=7Hz), 1.94–2.16(2H, m), 3.30(2H, t, J=7Hz), 4.07(4H, d, J=7Hz), 4.53(2H, t, J=7Hz), 6.88–7.02(2H, m), 7.19(1H, dd, J=5Hz, 1Hz), 7.46(1H, d, J=9Hz), 7.93(1H, dd, J=9Hz, 2Hz), 7.96(1H, d, J=2Hz), 8.18(1H, s). |

*IR was measured in CHCl$_3$ in principle.
**NMR was measured in CDCl$_3$ in principle.

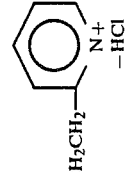

TABLE 7

| Compound No. | Structure [in Formula (I)] | | | | Yield | Property, m.p. (°C.) recrystallizing solvent | IR* (υcm⁻¹) | NMR** (δ ppm) |
|---|---|---|---|---|---|---|---|---|
| | R¹ | R² | R³ | —(CH₂)ₘ(Y)ₙX | | | | |
| 25 | —CO₂Et | H | H |  | 63 | Yellow crystals 137–140 (—) | (Nujol) 2205 1755 1710 | 1.25–1.55(1H, m), 1.70–1.90(4H, m), 4.00(2H, t, J=7Hz), 4.25–4.40(4H, m), 6.95–7.10(3H, m), 7.55(1H, d, J=9Hz), 7.78–7.90(2H, m), 8.17(1H, s). (CD₃OD:CDCl₃ = 1:1) |
| 26 | —CO₂Et | —CO₂Et | H |  | 47 | As free base 171–174 (—) | 2200 1770 1730 | 1.39(6H, t, J=7Hz), 2.95(2H, t, J=7Hz), 4.35(4H, q, J=7Hz), 4.47(2H, t, J=7Hz), 6.67(2H, d, J=9Hz), 7.07(2H, d, J=9Hz), 7.46(1H, d, J=10Hz), 7.86–7.98(2H, m), 8.14(1H, s). [Data as free base] |
| 27 | —CO₂Et | —CO₂Et | H |  | 60 | Colorless oil | 1730 1775 2250 | 1.39(6H, t, J=7Hz), 4.28–4.45(6H, m), 4.67(2H, t, J=5Hz), 6.90–7.05(2H, m), 7.25–7.35(3H, m), 7.46(1H, d, J=8Hz), 7.90–8.00(2H, m), 8.23(1H, s). |
| 28 | —CO₂Et | —CO₂Et | H |  | 60 | 83–84 colorless crystals | 1730 1770 2250 | 1.39(6H, t, J=7Hz), 4.35(4H, q, J=7Hz), 4.98(2H, dd, J=1Hz, 7Hz), 6.35(1H, dt, J=16Hz, 7Hz), 6.76(1H, d, J=16Hz), 7.27–7.47(6H, m), 7.90–7.96(2H, m), 8.21(1H, s). |

*IR was measured in CHCl₃ in principle.
**NMR was measured in CDCl₃ in principle.

TABLE 8

| Compound No. | Structure [in Formula (I)] R¹ | R² | R³ | —(CH₂)ₘ(Y)ₙX | Yield | Property, m.p. (°C.) recrystallizing solvent | IR* (υcm⁻¹) | NMR** (δ ppm) |
|---|---|---|---|---|---|---|---|---|
| 29 | —CO₂Et | —CO₂Et | —CO₂Et | thiophene—CH₂CH₂— | 57 | 68-59 CHCl₃-hexane | 1730 1780 2230 | 1.31-1.48(9H, m), 3.29(2H, t, J=7Hz), 4.27-4.43(6H, m), 4.53(2H, t, J=7Hz), 6.91-7.03(2H, m), 7.19(1H, dd, J=5Hz, 1Hz), 7.86-7.98(2H, m), 8.14(1H, s). |
| 30 | —CONHEt | —CONHEt | H | thiophene—CH₂CH₂— | 59 | 150-152 n-hexane-CHCl₃ | 2200 1750 | 1.23(6H, t, J=7Hz), 3.20-3.45(6H, m), 4.52(2H, t, J=7Hz), 6.91-7.00(2H, m), 7.19(1H, d, J=3Hz), 7.39(1H, d, J=10Hz), 7.82-7.95(2H, m), 8.17(1H, s). |
| 31 | —CONMe₂ | —CONMe₂ | H | thiophene—CH₂CH₂— | 44 | 215-217 (—) | 3500 2200 1725 1600 | 3.07(3H, s), 3.18 (3H, s), 3.29(2H, t, J=7Hz), 4.51(2H, t, J=7Hz), 6.91-7.00(2H, m), 7.08-7.25(2H, m), 7.72(1H, brs), 7.87(1H, brs), 8.12(brs). |
| 32 | —CONMe₂ | H | H | thiophene—CH₂CH₂— | 73 | 142-143 (—) | 2225 1730 | 3.03(6H, s), 3.08(3H, s), 3.09(3H, s), 3.29(2H, t, J=7Hz), 4.52(2H, t, J=7Hz), 6.92-7.02(2H, m), 7.18-7.24(1H, m), 7.42(1H, d, J=9Hz), 7.84(1H, dd, J=9.1Hz), 7.94(1H, brs), 8.18(1H, s). |
| 33 | —CONMe₂ | —CO₂Et | H | thiophene—CH₂CH₂— | 64 | 78 (—) | 2225 1770 1730 | 1.39(3H, t, J=7Hz), 3.02(3H, s), 3.09(1H, s), 3.29(2H, t, J=7Hz), 4.36(2H, q, J=7Hz), 4.53(2H, t, J=7Hz), 6.90-7.00(2H, m), 7.20(1H, m), 7.41(1H, d, J=9Hz), 7.86(1H, dd, J=9.1Hz), 7.94(1H, brs), 8.18(1H, s). |

*IR was measured in CHCl₃ in principle.
**NMR was measured in CDCl₃ in principle.

TABLE 9

| Compound No. | Structure [in Formula (I)] | | | | Yield | Property, m.p. (°C.) recrystallizing solvent | IR* (υcm⁻¹) | NMR** (δ ppm) |
|---|---|---|---|---|---|---|---|---|
| | R¹ | R² | R³ | –(CH₂)ₘ(Y)ₙX | | | | |
| 34 | –C(=O)– | | H | –CH₂CH₂–[thiophene] | 22 | 106–108 CHCl₃-hexane | 1730 1860 2225 | 3.30(2H, t, J=7Hz), 4.54(2H, t, J=7Hz), 6.86–7.08(2H, m), 7.19(1H, dd, J=5Hz, 1Hz), 7.40(1H, d, J=9Hz), 7.81(1H, dd, J=9Hz, 2Hz), 8.06(1H, d, J=2Hz), 8.22(1H, s). |
| 35 | –C(=O)– | | H | –CH₂CH₂–[phenyl] | 35 | 134–135 CHCl₃-hexane | 1860 | 1730 3.08(2H, t, J=7Hz), 4.53(2H, t, J=7Hz), 7.15–7.50(6H, s), 7.79(1H, dd, J=8Hz, 1Hz), 2225 8.05(1H, d, J=1Hz), 8.18(1H, s). |
| 36 | –C(=O)– | | H | –[phenyl] | 49 | 180–181 CHCl₃-hexane | 1745 1860 2225 | 7.08–7.62(6H, m), 7.88(1H, dd, J=9Hz, 2Hz), 8.14(1H, d, J=2Hz), 8.37(1H, s). |

*IR was measured in CHCl₃ in principle.
**NMR was measured in CDCl₃ in principle.

We claim:

1. A caffeic acid compound represented by the following formula (I):

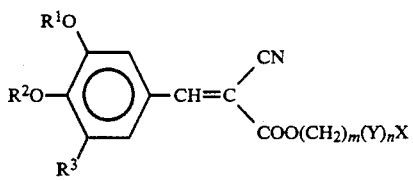

wherein one of $R^1$ and $R^2$ is a member selected from the group consisting of a hydrogen atom, a $C_1$-$C_6$ alkyl group, a group —$CO_2R^4$, $R^4$ representing a $C_1$-$C_{12}$ alkyl group, a $C_6$-$C_{10}$ aryl group, a hydrogen atom or a $C_7$-$C_6$ alkyl group and $R^6$ representing a hydrogen atom or a $C_1$-$C_6$ alkyl group, and the other of $R^1$ and $R^2$ is the group —$CO_2R^4$ or the group —$CONR^5R^6$, or $R^1$ and $R^2$ are coupled together to represent a 5-membered ring so formed, Y represents a vinylene group, an oxygen atom or a sulfur atom, X represents a substituted or unsubstituted $C_6$-$C_{10}$ aryl group, or a substituted or unsubstituted $C_7$-$C_{12}$ aralkyl group, m means an integer of 0–8, n denotes an inter of 0 or 1, and $R_3$ represents a hydrogen atom, a hydroxyl group, a group —$OCO_2R^7$, $R^7$ representing a $C_1$-$C_{12}$ alkyl group, a $C_6$-$C_{10}$ group, a hydrogen atom or a $C_7$-$C_{12}$ aralkyl group, or a group —$OCONR^8R^9$, $R^8$ representing a $C_1$-$C_6$ alkyl group and $R^9$ representing a hydrogen atom or a $C_1$-$C_6$ alkyl group, or a pharmaceutically acceptable salt thereof.

2. A therapeutic agent for a disease of the circulatory system, comprising as its active ingredient, and effective amount of the compound according to claim 1.

* * * * *